(12) United States Patent
Hamann et al.

(10) Patent No.: US 9,869,623 B2
(45) Date of Patent: Jan. 16, 2018

(54) PROCESS FOR EVALUATION OF DELAMINATION-RESISTANCE OF HARD COATINGS ON METAL SUBSTRATES

(71) Applicant: Apple Inc., Cupertino, CA (US)

(72) Inventors: Eric W. Hamann, Santa Clara, CA (US); William A. Counts, Sunnyvale, CA (US); James A. Curran, Morgan Hill, CA (US)

(73) Assignee: Apple Inc., Cupertino, CA (US)

( * ) Notice: Subject to any disclaimer, the term of this patent is extended or adjusted under 35 U.S.C. 154(b) by 312 days.

(21) Appl. No.: 14/678,881

(22) Filed: Apr. 3, 2015

(65) Prior Publication Data

US 2016/0290917 A1   Oct. 6, 2016

Related U.S. Application Data

(63) Continuation of application No. PCT/US2015/024349, filed on Apr. 3, 2015.

(51) Int. Cl.
 *G01N 3/48* (2006.01)
 *G01N 19/04* (2006.01)
 *G01N 3/42* (2006.01)

(52) U.S. Cl.
 CPC .............. *G01N 3/48* (2013.01); *G01N 3/42* (2013.01); *G01N 19/04* (2013.01); *G01N 2203/0286* (2013.01)

(58) Field of Classification Search
 CPC ............ G01N 19/04; G01N 3/42; G01N 3/48
 See application file for complete search history.

(56) References Cited

U.S. PATENT DOCUMENTS 2,692,851 A * 10/1954 Burrows ............... C25D 11/08
                                                      205/148
3,388,050 A    6/1968 Wainer et al.
3,411,994 A   11/1968 Wainer et al.
4,039,355 A    8/1977 Takahashi et al.
              (Continued)

FOREIGN PATENT DOCUMENTS

CH        691064 A5    4/2001
EP       2301760 A2    3/2011
              (Continued)

OTHER PUBLICATIONS

Brock, Thomas, et al. "European Coatings Handbook", 2000, Curt R. Vincentz, pp. 374-376.*

(Continued)

*Primary Examiner* — Paul West
(74) *Attorney, Agent, or Firm* — Downey Brand LLP

(57) ABSTRACT

This disclosure relates to rapid and repeatable tests that can be used to evaluate the interfacial adhesion of coatings to substrates. In particular embodiments, tests are used to assess the resistance of anodic oxides to delamination from aluminum substrates. The tests can be conducted using standard hardness test equipment such as a Vickers indenter, and yield more controlled, repeatable results than a large sample of life-cycle tests such as rock tumble tests. In particular embodiments, the tests involve forming an array of multiple indentations within the substrate such that stressed regions where the coating will likely delaminate are formed and evaluated.

20 Claims, 9 Drawing Sheets

(56) References Cited

U.S. PATENT DOCUMENTS

| | | | |
|---|---|---|---|
| 4,066,516 | A | 1/1978 | Sato |
| 4,483,751 | A | 11/1984 | Murayama et al. |
| 4,518,468 | A | 5/1985 | Fotland et al. |
| 4,606,796 | A | 8/1986 | Hanazima et al. |
| 4,631,112 | A | 12/1986 | Usui et al. |
| 4,856,326 | A | 8/1989 | Tsukamoto et al. |
| 4,894,127 | A | 1/1990 | Wong et al. |
| 4,987,766 | A * | 1/1991 | Brar ............... G01N 3/303 73/12.13 |
| 5,066,368 | A | 11/1991 | Pasqualoni et al. |
| 5,078,845 | A | 1/1992 | Kunughara et al. |
| 5,277,788 | A | 1/1994 | Nitowski et al. |
| 5,336,341 | A | 8/1994 | Maejima et al. |
| 5,705,225 | A | 1/1998 | Dornfest et al. |
| 6,027,629 | A | 2/2000 | Hisamoto et al. |
| 6,339,958 | B1 | 1/2002 | Tsui et al. |
| 6,581,446 | B1 | 6/2003 | Deneuville et al. |
| 7,527,872 | B2 | 5/2009 | Steele et al. |
| 7,732,056 | B2 | 6/2010 | Bhatnagar et al. |
| 8,691,403 | B2 | 4/2014 | Amakusa et al. |
| 9,359,686 | B1 | 6/2016 | Curran et al. |
| 2003/0196907 | A1 | 10/2003 | Viola |
| 2004/0004003 | A1 | 1/2004 | Hesse |
| 2005/0061680 | A1 | 3/2005 | Dolan |
| 2006/0019035 | A1 | 1/2006 | Munz et al. |
| 2008/0274375 | A1 | 11/2008 | Ng et al. |
| 2008/0283408 | A1 | 11/2008 | Nishizawa |
| 2009/0050485 | A1 | 2/2009 | Wada et al. |
| 2009/0233113 | A1 | 9/2009 | Hisamoto et al. |
| 2010/0024534 | A1 | 2/2010 | Li et al. |
| 2010/0264036 | A1 | 10/2010 | Hatanaka et al. |
| 2010/0326839 | A1 | 12/2010 | Morikawa et al. |
| 2011/0252874 | A1 | 10/2011 | Patten et al. |
| 2011/0297319 | A1 | 12/2011 | Chen et al. |
| 2012/0298513 | A1 | 11/2012 | Shimao et al. |
| 2013/0008796 | A1 | 1/2013 | Silverman et al. |
| 2013/0153427 | A1 | 6/2013 | Tatebe |
| 2013/0156635 | A1 | 6/2013 | Lee et al. |
| 2013/0319872 | A1 | 12/2013 | Woodhull et al. |
| 2014/0083861 | A1 | 3/2014 | Askin et al. |
| 2016/0060783 | A1 | 3/2016 | Curran et al. |
| 2016/0237586 | A1 | 8/2016 | Curran et al. |
| 2016/0289858 | A1 | 10/2016 | Curran et al. |
| 2017/0051425 | A1 | 2/2017 | Curran et al. |
| 2017/0051426 | A1 | 2/2017 | Curran et al. |
| 2017/0088917 | A1 | 3/2017 | Curran et al. |

FOREIGN PATENT DOCUMENTS

| | | |
|---|---|---|
| JP | H0347937 A | 2/1991 |
| JP | 2000313996 | 11/2000 |
| JP | 2009209426 A | 9/2009 |
| KR | 1020120021616 | 3/2012 |
| KR | 101235350 B1 | 2/2013 |

OTHER PUBLICATIONS

PCT Application No. PCT/US2014/053595—International Search Report & Written Opinion dated Jun. 24, 2015.

Habazaki et al., "Nanoscale Enrichments of Substrate Elements in the Growth of Thin Oxide Films", Corrosion Science, vol. 39, No. 4, pp. 731-737, 1997.

Vesborg et al., "Addressing the terawatt challenge: scalability in the supply of chemical elements for renewable energy," RSC Advances, 2, pp. 7933-7947, 2012.

U.S. Appl. No. 14/474,021—Non Final Office Action dated Aug. 27, 2015.

European Patent Application No. 16150283.6—European Search Report dated Jun. 9, 2016.

PCT Application No. PCT/U52015/025000—International Search Report and Written Opinion dated Jan. 26, 2016.

Garcia-Vergara, S. et al; "Morphology of enriched alloy layers in an anodized Al—Cu alloy" Applied Surface Science, 205 (2003),p. 121-127.

Alwitt, R.S. and R.C. McClung , "Mechanical Properties of Anodized Aluminum Coatings"; Proceedings of the SUR/FIN7 '92, American Electroplaters and Surface Finishers Society, Atlanta, Georgia, Jun. 1992.

Yann Goueffon et al., "Study of Degradation Mechanisms of Black Anodic Films in Simulated Space Environment" URL: http://webcache.googleusercontent.com/search?q=cache:fsJq5LjVTVIJ:esmat.esa.int/materials_news/isme09/pdf/6-Contamination/S8%2520-%2520Goueffon.pdf+&cd=1&hl=en&ct=clnk&gl=us.

Henkel Corporation "BONDERITE M-ED 9000 Anodizing Seal (Known as Anoseal 9000)" Technical Process Bulletin Issued Jun. 10, 2013.

Ling Hao and B. Rachel Cheng., "Sealing Processes of Anodic Coatings—Past, Present, and Future", Metal Finishing, vol. 98, Issue 12, Dec. 2000, p. 8-18.

PCT Application No. PCT/US2015/010736—International Search Report & Written Opinion dated Nov. 29, 2015.

PCT Application No. PCT/US2015/024349—International Search Report & Written Opinion dated Dec. 17, 2015.

International Patent Application No. PCT/US2016/043256—International Search Report and Written Opinion dated Oct. 12, 2016.

* cited by examiner

PROCESS FOR EVALUATION OF DELAMINATION-RESISTANCE OF HARD COATINGS ON METAL SUBSTRATES

CROSS-REFERENCE TO RELATED APPLICATION

This is a continuation of International Application PCT/US15/24349, with an international filing date of Apr. 3, 2015, entitled "PROCESS FOR EVALUATION OF DELAMINATION-RESISTANCE OF HARD COATINGS ON METAL SUBSTRATES", the disclosure of which is incorporated herein by reference in its entirety.

FIELD

The described embodiments relate generally to evaluating hard coatings on surfaces of articles. More particularly, the present embodiments relate to methods for evaluating the adhesion strength and delamination-resistance of a coating on a surface of an article.

BACKGROUND

Surface coatings are used on consumer devices to protect the surface and enhance the aesthetics and texture of the device. One example of such a coating is anodizing a metal surface. Anodizing a metal surface converts a portion of the metal surface into an anodic oxide, thereby creating an anodic oxide layer. The anodic oxide layer may be harder than the underlying metal substrate.

While a coating may be harder than the underlying substrate, a relatively stiff coating is susceptible to becoming detached from the substrate when the article is subjected to mechanical stresses. Thick, stiff coatings, on relatively compliant substrates are particularly susceptible to delamination, and since properties such as stiffness and thermal expansion are often strongly correlated, this scenario can be exacerbated by thermally induced strain.

Various mechanical tests exist for evaluating the interfacial strength and interfacial adhesion of the coatings. These include pull-off tests, thermal cycling and thermal shock, and techniques such as four-point bend delamination for propagating delamination under steady state and measuring interfacial adhesion energies. One common (though more qualitative) test for the adhesive strength of a coating of consumer products is the "rock tumble" test. This test is performed by tumbling the article having the coating for an extended time with items the article will typically encounter during its expected lifetime. However, these tests are random in nature, and must be repeated multiple times for each coating to be tested to extrapolate a statistically significant result. In addition, these tests may have inherent limitations, such as the strength of adhesives used for bonding in pull-off tests, or require very specific sample geometries, such as is the case in bend delamination tests. For these reasons, incremental improvements in layered structure strength and adhesion are difficult to evaluate.

SUMMARY

This paper describes various embodiments that relate to coatings and methods of testing the adhesion strength of these coatings. The methods described can be used to precisely and reliably evaluate the integrity and expected lifetime durability of a coating.

According to one embodiment, a method of testing an adhesion strength between a coating and a substrate is described. The method includes creating a pre-defined pattern of indentations using an impacting agent arranged to deliver a pre-defined impact force, and a corresponding pattern of applied stresses, to the coating and substrate at specified locations. When the adhesion strength is less than a delamination force and its corresponding pattern of applied stresses, at least a portion of the coating delaminates from the substrate at a stressed region of the coating defined in part by the specified locations and associated with the delamination force.

According to another embodiment, a method of method of testing an adhesion strength between a coating a substrate is described. The method includes forming a pattern of indentations using an indentation tool arranged to deliver a pre-defined impact force on the coating and the substrate. Forming the pattern includes creating indentations within the coating and the substrate by moving the indentation tool along a surface of the coating a pre-defined distance between the indentations such that the indentations are equidistantly spaced. A delamination force is formed within stressed regions between the indentations. The coating delaminates from the substrate at the stressed regions when the delamination force is greater than the adhesion strength.

According to a further embodiment, an apparatus for determining an adhesion strength between a coating and a substrate is described. The apparatus includes an indentation tool arranged to create a pattern of indentations within the coating and the substrate. The indentation tool includes an impactor arranged to form an indentation at a specified location on the surface of the coating by delivering a pre-defined impact force at the specified location on the coating and the substrate. When the adhesion strength is less than a delamination force, at least a portion of the coating delaminates from the substrate at a stressed region of the coating defined in part by the specified locations and associated with the delamination force.

BRIEF DESCRIPTION OF THE DRAWINGS

The disclosure will be readily understood by the following detailed description in conjunction with the accompanying drawings, wherein like reference numerals designate like structural elements.

DETAILED DESCRIPTION

Figure 1:
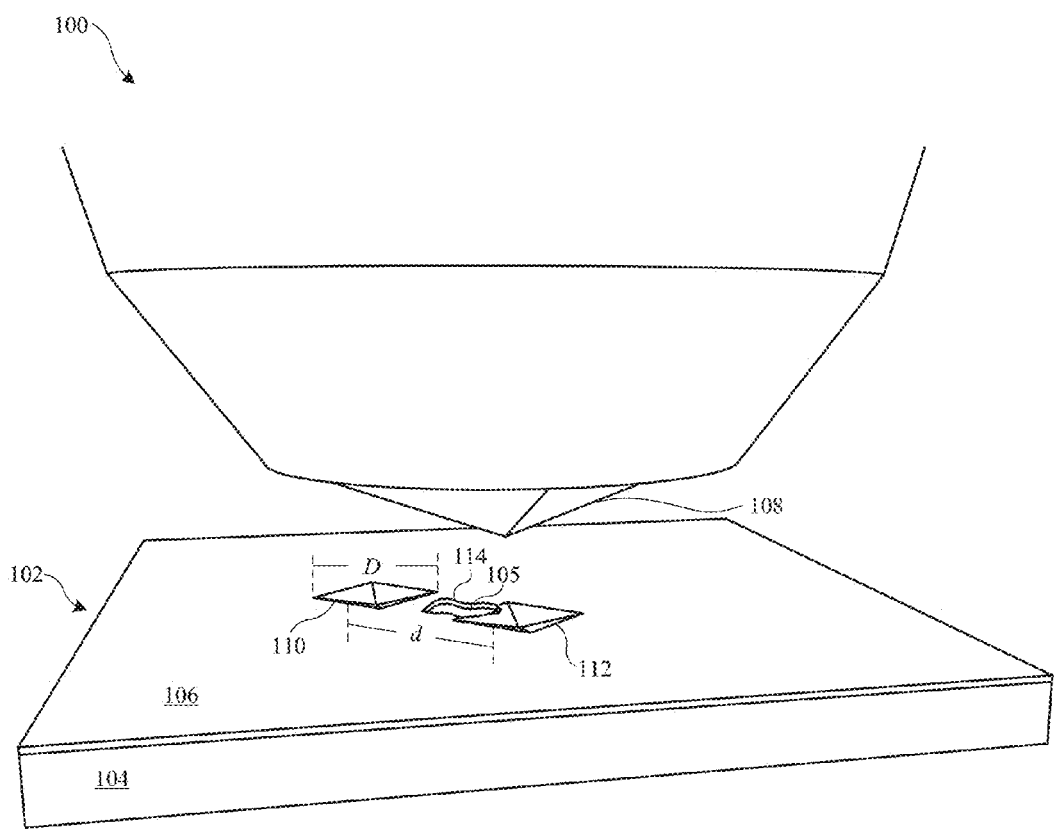
FIG. 1 shows a perspective view of an indentation tool and an indentation pattern on an article having two indentations and a resulting delamination of a coating in a stressed region formed between the indentations.

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

The following disclosure relates to methods of testing the adhesion strength of coating on a surface of substrate. There is a need in the art of coatings to test the adhesion of a coating to an underlying substrate, particularly where the coating is relatively stiff in relation to the underlying substrate. For example, coatings on surfaces of consumer devices are normally subjected to various mechanical and thermal stresses during the lifetime of the consumer devices. Coating spallation can occur when a coating is subjected to these stresses, which results in an undesirable surface finish.

As used herein, the terms "adhesive failure" or "detachment" of a coating or indeed a system of multiple coatings (such as a multilayered stack of coatings) are sometimes also described as "spallation" or "delamination". The latter term is used throughout this paper to refer to generally to failure of the interfacial adhesion of a coating. It should also be recognized that certain coatings or coating systems may fail at locations other than the immediate interface; for instance, due to crack propagation along an intermediate level, broadly parallel to the interface. Such failures, while not strictly interfacial, can have similar detrimental effects (such as the loss of a dye or seal layer) and are considered to lie within the scope of testing methods described herein. Thus, the terms "adhesive failure," "detachment," "spallation," and "delamination" are used interchangeably in this paper, and can refer broadly to adhesion failure of a coating at or near the interface between the coating and underlying substrate. Likewise, the terms "detachment force" and "delamination force" are used interchangeably, and can refer broadly to a force created at the coating and/or substrate that can cause detachment of the coating at or near the interface.

While various mechanical tests exist to evaluate the adhesion strength of coatings, these tests are imprecise in their results and thus require multiple samples to be evaluated over an extended period of time to extrapolate statistically significant results. As an example, a "rock-tumble" test that is routinely used requires multiple samples of a coating to be individually tumbled with various objects over an extended period of time to simulate the life expectancy of the coating. Due to the inherent randomness of this test, the results are unreliable and an improved method for testing the integrity of coatings is disclosed herein.

In some embodiments, testing the surface adhesion strength of a coating includes forming two or more indentations in the coating. In some cases the indentations extend through the coating and plastically deform the underlying substrate. The deformation of the substrate and the coating can induce a pattern of stresses in the coating, with stressed regions in the coating in areas between the indentations. This stressed state of the coating and/or substrate may exert a detachment or delamination force on the coating that can cause the coating to detach or delaminate from the substrate. The delamination force can be perpendicular to the substrate, coplanar to the substrate, or some combination of these directions.

In particular embodiments, the testing process involves applying a Vickers indenting tool normal to the surface of the coating a number of times to form a grid or array of indentations. The indentations are of such size as to produce substantial plastic deformation in the substrate material, and are spaced very closely such that the residual strain from each successive indentation interacts with each other. In some embodiments a square array of between three-by-three and five-by-five indentations are be used. Each indentation produces large interfacial shear strains between the coating and substrate, inducing controlled delamination. Subsequent, adjacent indentations help to promote spallation of the coating, and expose the substrate.

In other embodiments, the spacing of indents is not uniform, but is varied—either in progressively more widely spaced rows or columns, or with both row and column spacing progressively increasing. The applied force may be constant, or may also be progressively increased. Thus, a single pattern can produce multiple instances of various different stress states, and any observed pattern of coating spallation may be correlated to the pattern of applied stresses to determine a threshold for failure.

These and other embodiments are discussed below with reference to FIGS. 1-8. However, those skilled in the art will readily appreciate that the detailed description given herein with respect to these Figures is for explanatory purposes only and should not be construed as limiting.

The testing methods described herein can be used to rapidly, accurately, and controllably replicate conditions that induce delamination of a coating in-service, enabling rapid assessment of the relative delamination resistance of various different types of coatings. The testing methods can employ common laboratory equipment, and can be applicable to samples of any suitable geometry. The methods involve producing multiple indentations within the coating such that stressed regions are formed within coating. While single large indentations induce interfacial delamination, implementing a succession of adjacent of indentations with interacting stress fields form a pattern of spallation that can be analyzed.

In some embodiments, the process involves forming two or more indentations within a coated substrate. FIG. 1 shows a perspective view 100 of indentation tool 108 forming two indentations 110 and 112 within sample or article 102 in accordance with some embodiments. Article 102 includes substrate 104 and coating 106. An impacting agent or impactor, such as indentation tool 108 is pressed into the surface of article 102, plastically deforming coating 106 and substrate 104 of article 102, thus creating indentations 110 and 112. The force applied to coating 106 and substrate 104 can be a pre-defined amount of impact force such that each of indentations 110 and 112 are formed using the same amount of impact force. In some embodiments, indentations 110 and 112 formed by pressing indentation tool 108 under constant force for a predetermined period of time. In some embodiments, the constant force is exerted for about 10 seconds. In other embodiments, a constant force is exerted on indentation tool 108 for between 1 and 30 seconds. The force applied by indentation tool 108 can vary depending on the hardness of coating 106 and substrate 104, as well as a desired depth of indentations 110 and 112. In some embodiments where coating 106 is an anodic oxide material and substrate is metal, the force used to form indentations 110 and 112 is in the range of 500 grams to 50 kilograms. In other embodiments, less force is used. For example, in a particular embodiment, the force used to form indentations 110 and 112 is about 10 kilograms.

When indentation 110 is formed, a corresponding residual stress is formed within article 102 proximate to indentation 110. Likewise, when indentation 112 is formed, a corresponding residual stress is formed within article 102 proximate to indentation 112. The residual strain proximate to each of indentations 110 and 112 is created when substrate 104 and coating 106 are plastically deformed, creating a large interfacial shear strain between substrate 104 and coating 106. If indentations 110 and 112 are spaced close enough to each other, the residual strains associated with each of indentations 110 and 112 overlap to form stressed region 114 of coating 106. In this way, coating 106 is placed in a stressed state. This creates a corresponding delamination force within stressed region 114. That is, the residual stress associated with each of indentations 110 and 112 can cooperate to form stressed region 114 and a corresponding delamination force. If the delamination force is greater than an adhesion strength between coating 106 and substrate 104, a portion of coating 106 delaminates from substrate 104 exposing portion 105 of substrate 104. Put another way, when an adhesion strength between coating 106 and substrate 104 is insufficient to withstand the detachment or delamination force created by the stressed state, at least a portion of coating 106 detaches or delaminates from substrate 104 at stress region 114. Delamination is most likely to occur at or near stressed region 114 since this is where most of the delamination force is concentrated.

It is important to note that this type of delamination is generally avoided in standard hardness testing (e.g., Vickers hardness testing) where indentations are typically spaced apart at least 5 to 10 times the dimension of the residual deformation as a separation between indentations in order to avoid strain interactions. That is, it is generally undesirable to form stressed region 114 in conventional hardness testing techniques.

The distance d between indentations 110 and 112, as well as the amount of force applied to form indentations 110 and 112, can be chosen so as to provide repeatable results across multiple samples. For example, distance d can be chosen so as to optimize overlap and cooperation of the residual stresses created by indentations 110 and 112. In this way, controlled delamination and repeatable results can be achieved. In some embodiments, distance d is measured relative to diameter D of each of indentation 110 and indentation 112. If indentations 110 and 112 are the same size, diameter D of indentations 110 and 112 are the same. If indentations 110 and 112 are of different sizes, diameter D can refer to an average diameter of indentations 110 and 112. In some embodiments, diameter D measured from opposing corners of the indentations 110 and 112 and distance d between indentations 110 and 112 is measured from the center of each of indentations 110 and 112. According to some embodiments, measurable and repeatable results are accomplished when distance d is less than three times the diameter D of indentations 110 and 112.

The testing methods described herein are well suited for testing adhesion of anodic oxide layers since anodic oxides are generally stiffer than the corresponding underlying metal substrate, which is generally more compliant. Thus, in some embodiments substrate 104 is an anodizable metal material and coating 106 is a corresponding anodic oxide layer. For example, substrate 104 can be made of aluminum or aluminum alloy and coating 106 can be made of aluminum oxide. In some embodiments, article 102 corresponds to a consumer product having an anodized metal portion, such as a housing for an electronic device like a mobile phone, tablet device, laptop, or other computing device or electronic accessory. However, the testing methods described herein are not limited to use on anodic oxide layers and can be used to test adhesion strengths of any suitable type of coating. Thus, substrate 104 and coating 106 can be made of any suitable materials. For example, coating 106 can be made of a material that is formed using a physical vapor deposition (PVD) process. In other embodiments, the coating 106 is plated layer, such as a plated nickel, chrome, or other metal layer. In some embodiments, coating 106 includes multiple layers.

In some embodiments, indentation tool 108 is diamond indenter as part of a Vickers hardness testing apparatus. However, indentation tool 108 can be made of any suitable material harder than substrate 104 and coating 106. Indentation tool 108 has a square-based pyramid shape; however, indentation tool 108 can have any suitable shape and size. In some embodiments, the tip of indentation tool 108 is pressed into the surface of the article 102 substantially perpendicular with respect the surface of the article 102 forming substantially symmetric indentations 110 and 112. In some embodiments, the force used to form indentation 110 is equal to the force used to form indentation 112. In other embodiments, the force used to form indentation 110 is larger or smaller than the force used to form indentation 112.

The amount of delamination is associated with the area and number of exposed portions 105, which can be evaluated visually or by optical microscopy (if there is sufficient optical contrast between coating 106 and the substrate 104), and/or by electrical continuity testing or electron microscopy (if there is limited optical contrast). For example, a dyed anodic oxide coating on an aluminum alloy substrate can generally be detectable using optical microscopy techniques.

Figure 2A:
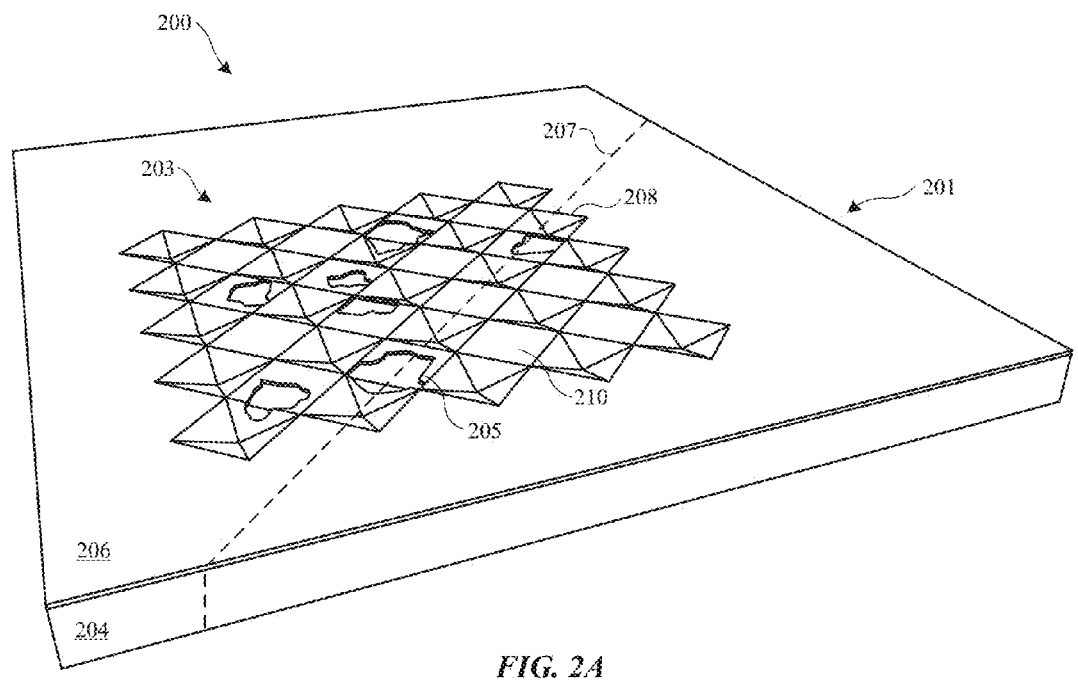
FIGS. 2A and 2B show perspective views of an indentation pattern on an article having multiple indentations arranged in a grid.
Figure 2B:
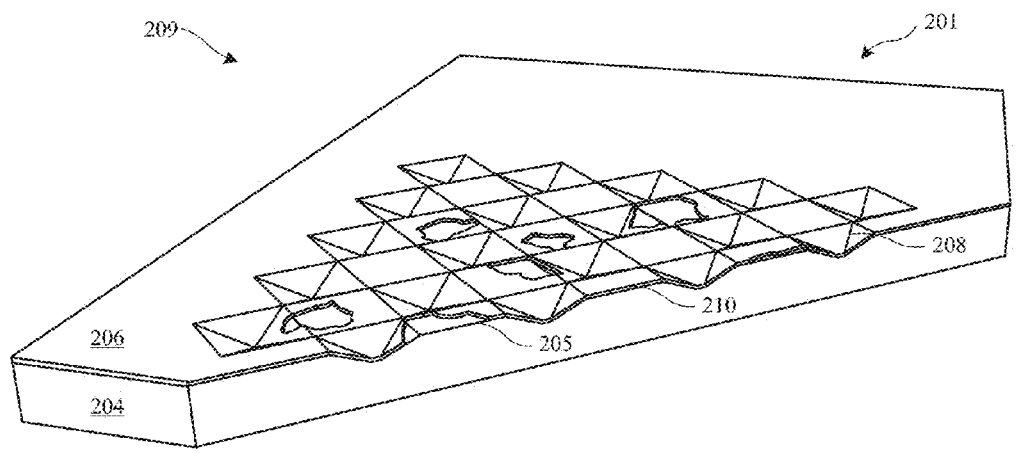

In some embodiments, more than two indentations are formed in a substrate such that the indentations form a pattern in the substrate. FIGS. 2A and 2B show perspective views of an indentation pattern 203 on sample or article 201, in accordance with some embodiments. FIG. 2A shows perspective view 200 of indention pattern 203 on an article 201. FIG. 2B shows perspective cross-sectional view 209 of article 201 as indicated by reference line 207 in FIG. 2A. Indentation pattern 203 is an array or grid of indentations 208 separated from each other by a pre-defined distance chosen to provide substantially the same delamination force at stressed regions 210 positioned between indentations 208. One can also view stressed regions 210 as different portions of a combined stressed region formed within article 201 by indentation pattern 203. In the instant case, indentation pattern 203 is an array or grid of indentations 208 arranged in five rows and five columns, which can be referred to as a five-by-five indentation pattern with indentations 208 substantially equidistantly spaced. In some embodiments, indentations 208 are arranged such that the corners of each indentation 208 are in contact with or proximate to the corners of adjacent indentations 208. Variations of other patterns can be formed, such as three-by-three or four-by-four indentation patterns. In some embodiments, optimal results were obtained using arrays of three-by-three or more (e.g., four-by-four, five-by-five, or greater). In some embodiments, substrate 204 has a minimum thickness of 0.4 mm with indentations 208 arranged in an array of a minimum of three-by-three in order to provide repeatable results.

Indentations 208 can each be formed using an indenting tool such as indentation tool 108 described above. Indentations 208 plastically deform substrate 204 and coating 206 creating a pattern of stress in the substrate 204, in the coating 206, and at the interface between the substrate 204 and coating 206. A number of similarly stressed regions 210 of coating and interface are created, defined by the edges of surrounding indentations 208. As described above, a delamination force is formed within stressed regions 210 when stresses from adjacent indentations 208 overlap. When the delaminating force results in stresses that exceed an interfacial adhesion of coating 206 to substrate 204, a portion of coating 206 delaminates from substrate 204 and exposes portions 205 of substrate 204 at or near stressed regions 210. Note that stressed regions 210 are not directly pressed on by an indenter, yet experience a delamination force due to stresses from the adjacent, closely space indentations 208.

In some embodiments, indentation pattern 203 is formed in a sequential manner. That is, each indentation 208 is formed one at a time. This can be achieved, for example, by moving an indentation tool relative to article 201 in rows of predetermined linear tool paths until indentation pattern 203 is formed. In particular, a first row of indentations 208 is formed by moving the indentation tool in a linear direction in one direction. Subsequent second, third, fourth and fifth rows can be formed similarly. In other embodiments, indentation pattern 203 is formed in one indentation event where the indentation tool includes multiple protrusions that form all indentations 208 at once. Movement of the indentation tool can be controlled such that corners of adjacent indentations 208 contact each other or are proximate to each other. Precise movement and applied force of the indentation tool can be controlled by an electronic system, such as an electronic system described below with reference to FIG. 7. In some embodiments, the indentation tool should be controllable to and accuracy of within about 5 micrometers. In some embodiments for testing aluminum oxide coatings on aluminum alloy substrates, the indentation tool should be capable of applying at least a 10 kilogram-force load.

The extent of delamination of coating 206 has been well-correlated with interfacial adhesion of coating 206 to substrate 204 as evaluated by more conventional controlled four-point bend delamination tests or pull-off tests. However, in contrast to four-point bend delamination or pull-off tests, the sample geometry is not as constrained, and little or no sample preparation is required for the indentation test described herein. Also, unlike four-point bend delamination or pull-off tests, there is no limit imposed by the strength of adhesives. Furthermore, unlike other more conventional mechanical tests, relatively high interfacial shear strains are readily attained under indentation with loads of just a few kilograms. The damage induced by described test procedures are also very localized, enabling an accurate and complete quantitative appraisal within a single, high-resolution optical image.

Figure 2C:
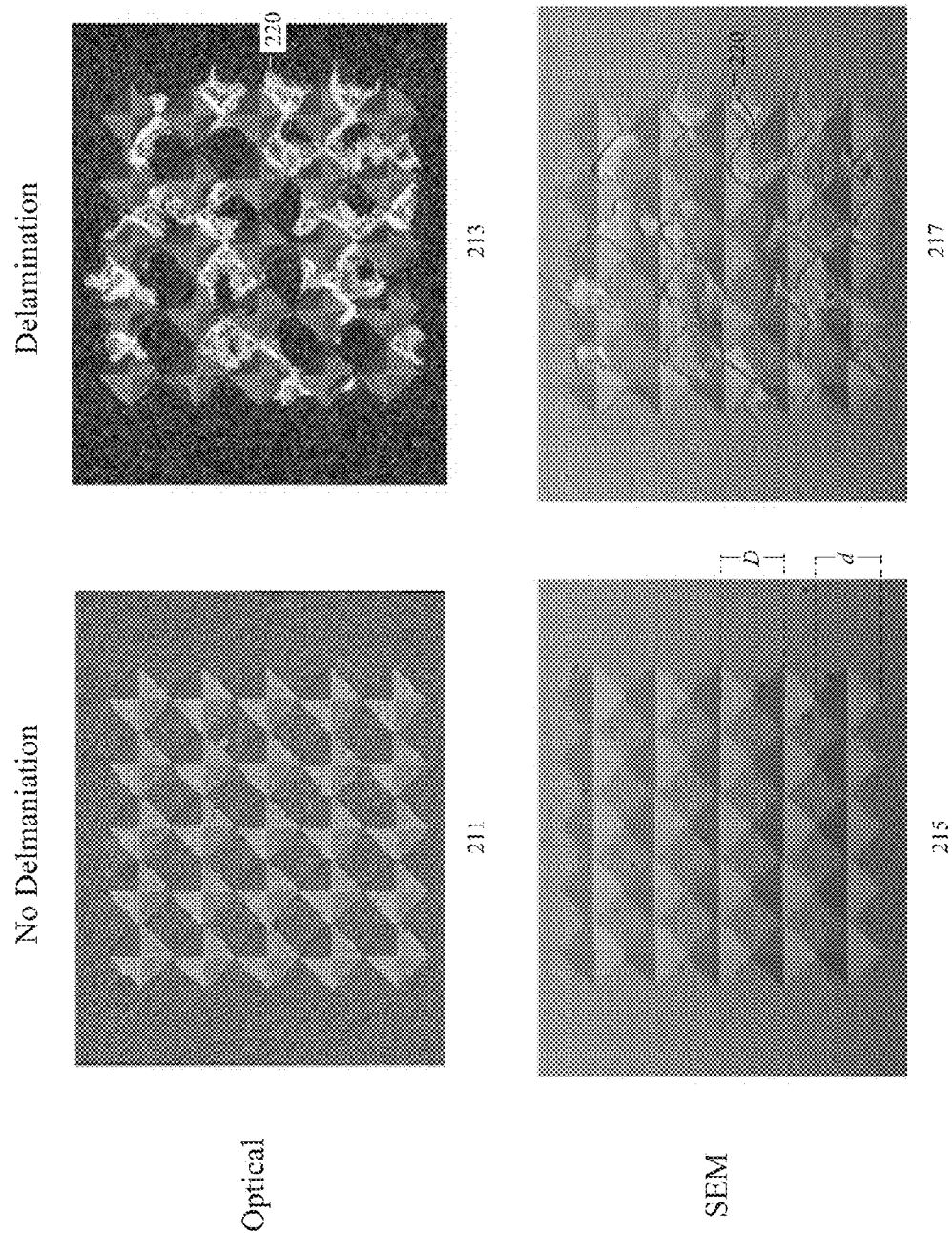
FIG. 2C shows optical and scanning electron microscope (SEM) images of five-by-five patterns of indentations.

FIG. 2C shows optical and scanning electron microscope (SEM) images of five-by-five patterns of indentations in accordance with described embodiments. FIG. 2C show images of articles with aluminum alloy substrates with aluminum oxide coatings. The top row of images (samples 211 and 213) shows light optical images using 400× magnification in a bright field with a camera. The bottom row of images (samples 215 and 217) shows SEM images using 60× magnification utilizing back scatter detection. The left column shows images of articles that experienced substantially no delamination after the five-by-five indentation test, and the right column shows images of articles that experienced significant delamination after the five-by-five indentation test. The diameters D of each indentation within the five-by-five patterns, as measured from centers of the indentations, are the same. The five-by-five pattern is arranged such that distance d between adjacent indentations is less than three times the diameter D. In some embodiments where the article is a 7000 series aluminum alloy (T5 or T6 temper), distance d between indentations is 350 micrometers±5 micrometers. In another embodiment where the article is a 6063 aluminum alloy (T5 or T6 temper), distance d between indentations is 420 micrometers±5 micrometers.

The images of FIG. 2C demonstrate that articles that experience delamination can be observed and distinguishable over articles that do not experience substantial delamination. In particular, samples 211 and 215 did not experience substantial delamination, whereas samples 213 and 217 did experience substantial delamination. As shown, delamination occurs mostly at or near stressed regions 220. In some embodiments, the amount of delamination is quantified such that data from a number of articles can be collected and analyzed. For example, an analysis can be performed based on counting the number of stressed regions 220 within a five-by-five sample that have delamination. The counting can be accomplished visually by an operator or automatically using a computer. In other embodiments, the total area of exposed substrate is measured.

Figure 3:
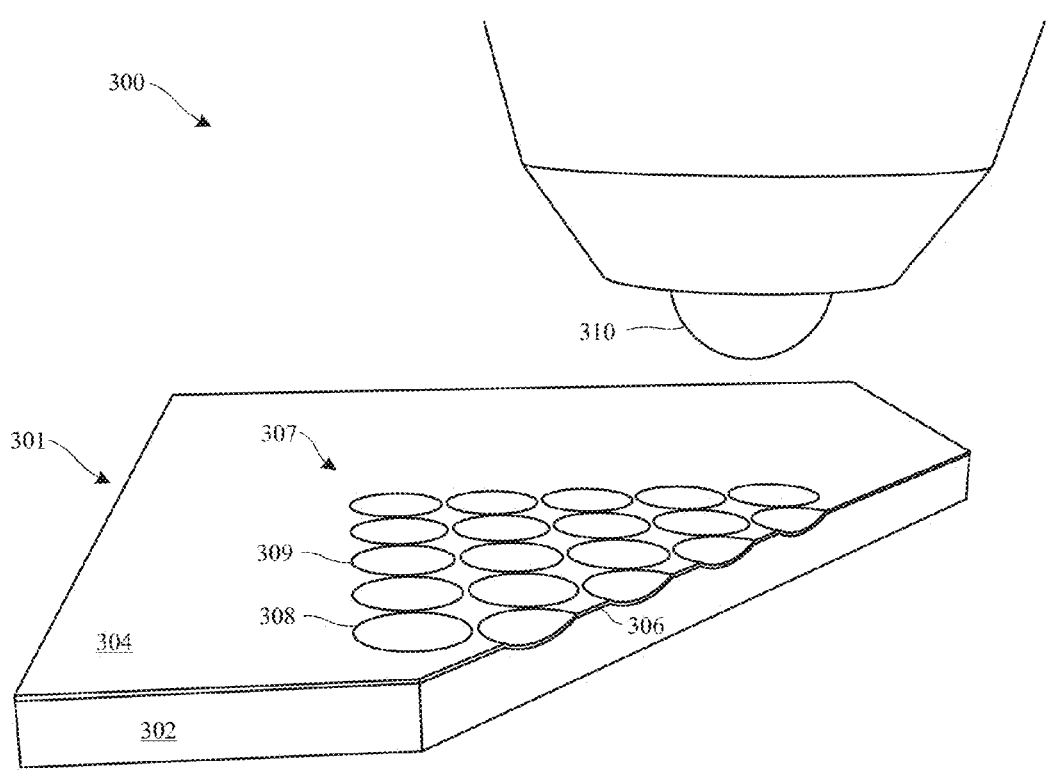
FIG. 3 shows a perspective cross-sectional view of an indentation pattern where the indentations are partially spherical.

The methods described herein are not limited to indentations having any particular size or shape. FIG. 3 shows a perspective cross-sectional view 300 of indentation tool 310 forming an indentation pattern 307 having indentations 308 within article 301 in accordance with some embodiments. Indentation tool 310 has spherical-based shape and thereby forms spherical-based or curved indentations 308. As with previously described indentations, forming indentations 308 plastically deforms coating 304 on the substrate 302 causing residual stress in the vicinity of indentations 308. The residual stresses overlap at stressed regions 306, corresponding to regions of article 301 likely to experience delamination. Stressed regions 306 are defined by edges 309 of indentations 308. In this case, stressed regions 306 have a rectangular shape, in some embodiments a square shape. Distances between indentations 308 (as measured from centers of indentations) can be chosen such that residual stresses cooperate to form a delamination force at stressed regions 306. In some embodiments, stressed regions 306 are continuous and flow from a first interstitial location to a proximate interstitial location. Other suitable variations of indentation shapes can include triangular-based and hexagonal-based shapes. In some embodiments, the pattern of indentations includes indentations having different shapes.

Figure 4:
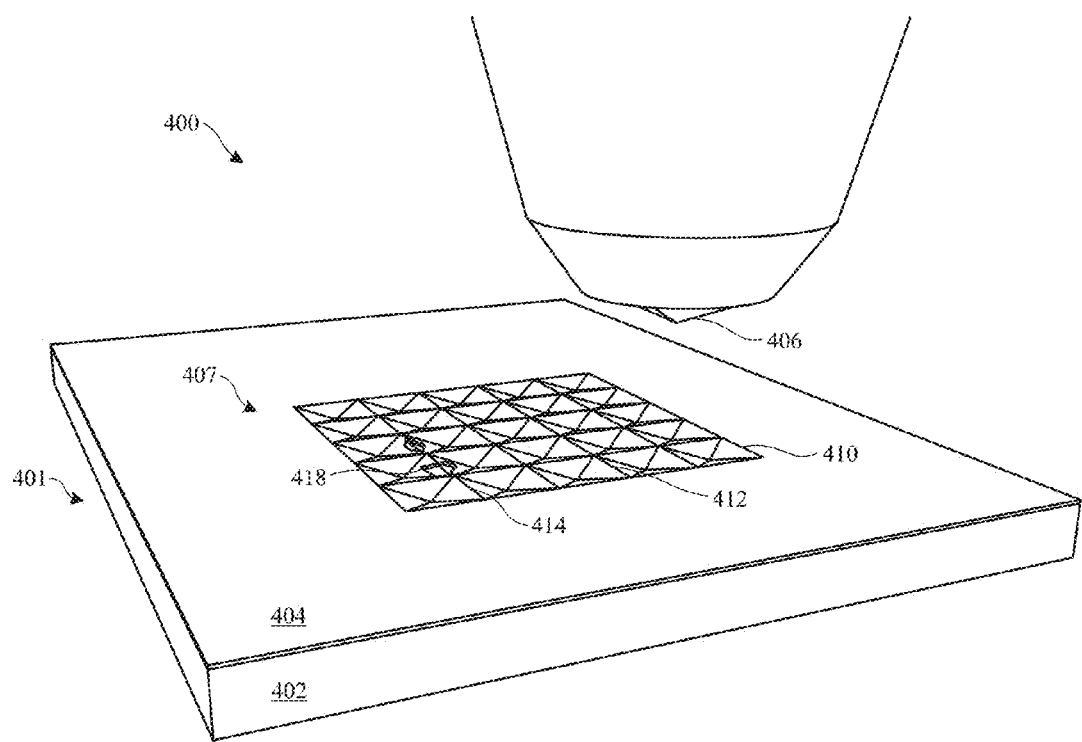
FIG. 4 shows a perspective view of an indentation pattern on an article with minimal spacing between indentations.

FIG. 4 shows perspective view 400 of indentation tool 406 forming indentation pattern 407 on article 401 in accordance with another embodiment. Indentation pattern 407 includes indentations 410 with minimal spacing there between, indicating that orientation and spacings between indentations 410 can vary. In some embodiments, indentations 410 are arranged such that stressed regions 414 created by indentations 410 occupy edges 412 of adjacent indentations 410. Delamination can occur at or near stressed regions 414 such that portions 418 of underlying substrate 402 are exposed through coating 404.

Figure 5A:
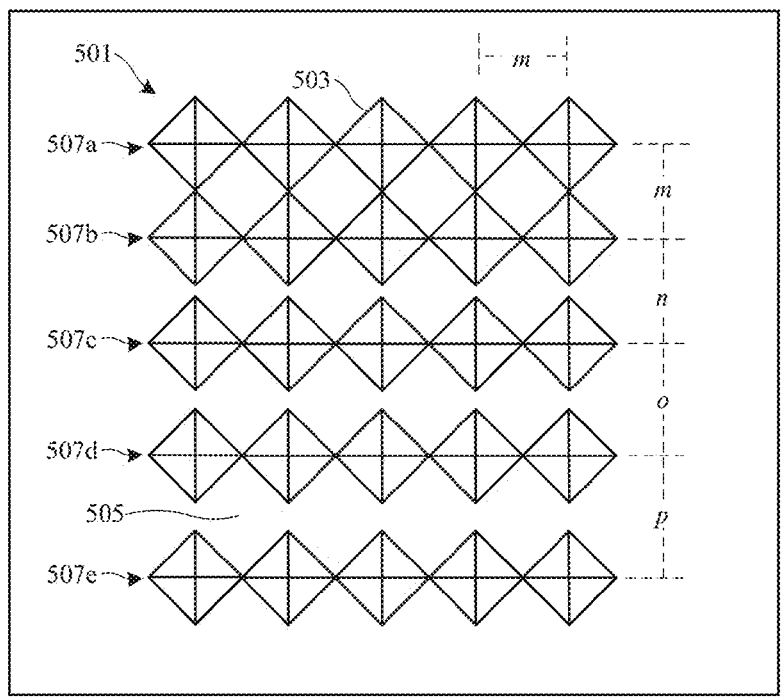
FIGS. 5A and 5B show top views of indentations patterns with varied spacing between indentations.
Figure 5B:
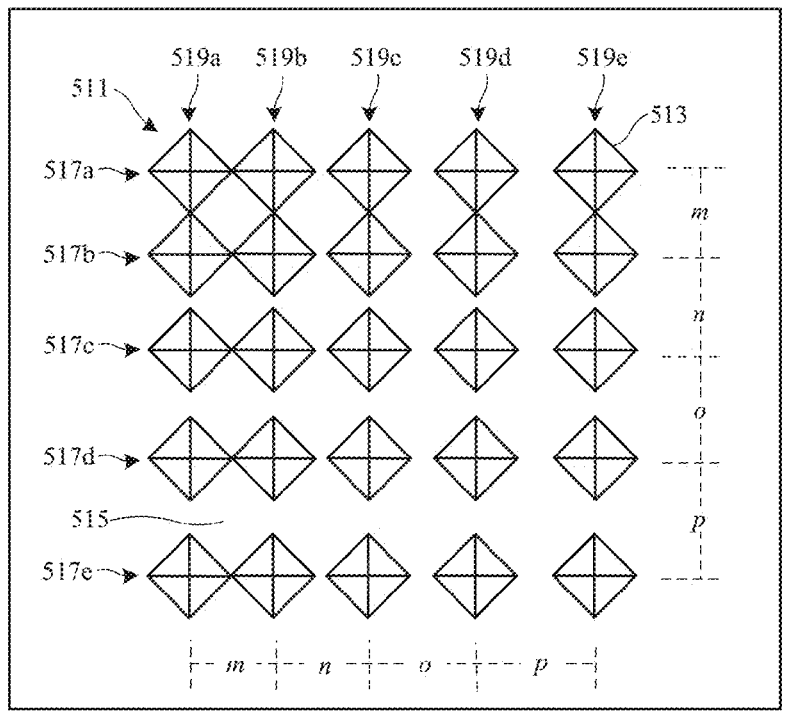

In some embodiments, indentation spacing and indentation force may be varied to produce a stress pattern in the coating with varied stress states. FIGS. 5A and 5B show top views of indentation patterns having varied indentation spacing and/or indentation force. FIG. 5A shows an indentation pattern 501 arranged in an array where spacing between indentations 503 is varied by row. As shown, spacings m, n, o, p between rows 507a, 507b, 507c, 507d, 507e vary progressively, producing multiple instances of various different stress states in stressed regions 505 created by indentations 503. Stress regions 505 between rows 507a and 507b can have similar stress states since they are separated by the same spacing m. Stress regions 505 between rows 507b and 507c can have similar stress states since they are separated by the same spacing n, but different than the stress states of stress regions 505 between rows 507a and 507b. Similarly, stress regions 505 between rows 507c, 507d, 507e separated by spacings o and p produce corresponding stress regions that are different than stress regions 505 between rows 507a and 507b separated by spacings n and m. In this way, varying stress regions 505 having different stress states can be formed within a single indentation pattern 501. Thus, indentation pattern 501 can be used to determine a stress threshold at which a coating will delaminate. For example, the detachment force created at stress regions between row 507a and 507b may be great enough to cause delamination; however, the detachment force created at stress regions between row 507d and 507d may not be great enough to cause delamination. In some embodiments, the force applied by the indentation tool can also be varied among indentations 503 within each of rows 507a, 507b, 507c, 507d, 507e, further varying the stress states of stress regions 505 between indentations 503. In other embodiments, spacings between columns are varied instead of between rows.

FIG. 5B shows an alternative indentation pattern 511 where indentations 513 are arranged in an array with spacing between rows and columns of indentations 513 are both varied progressively. In particular, spacings m, n, o, p between rows 517a, 517b, 517c, 517d, 517e vary progressively and spacings m, n, o, p between columns 519a, 519b, 519c, 519d, 519e vary progressively. This arrangement creates more varied stress states at stress regions 515 between indentations 513 across pattern 511. In some embodiments, the force applied by the indentation tool can also be varied among indentations 513 within indentations of each of rows 517a, 517b, 517c, 517d, 517e and/or columns 519a, 519b, 519c, 519d, 519e. These variations can be used to further determine a stress threshold for coating delamination. Although the spacing between rows and columns shown in FIGS. 5A and 5B are varied progressively, any suitable arrangement may be used that varies the spacing between indentations.

FIGS. 3, 4, 5A and 5B are shown to illustrate that the indentation methods described herein can use any suitable size, shape, orientation and distance (spacing) between indentations. These examples, however, are not meant to exclude other variations that may be implemented within the scope of the embodiments presented herein. In some embodiments, the shape, orientation, size and distance between indentations are chosen to result in providing repeatable results for a number of articles having similar or different coatings.

Figure 6:
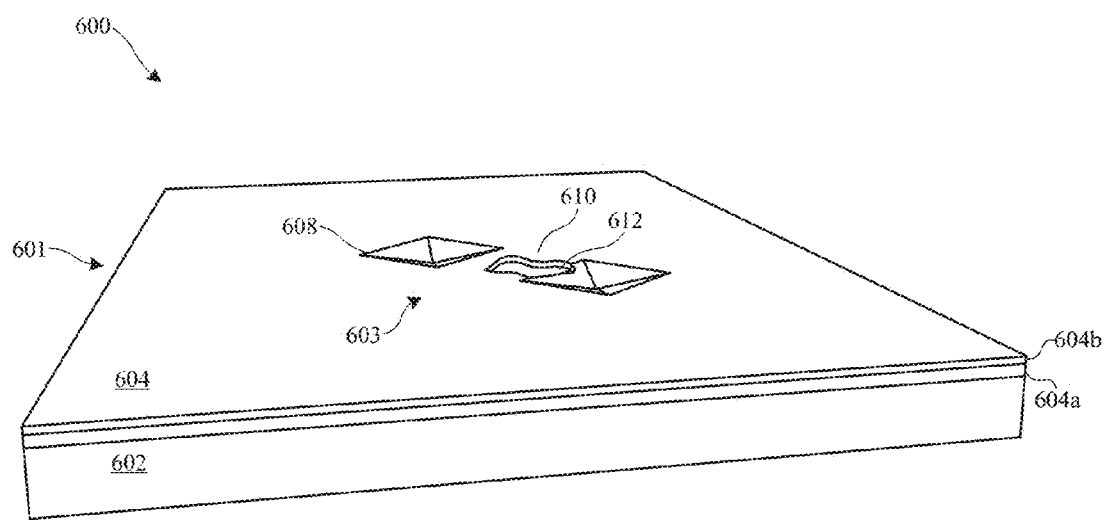
FIG. 6 shows a perspective view of an indentation pattern on an article having multiple coatings.

FIG. 6 shows a perspective view 600 of indentation pattern 603 on an article 601 having coating 604 with multiple layers. In particular, coating 604 includes first layer 604a and second layer 604b. First layer 604a can correspond, for example, to a first material deposited onto substrate 602 using a first deposition process and second layer 604b can correspond to a second material deposited on first layer 604a using a subsequent second deposition process. In other embodiments, coating 604 includes more than two layers 604a and 604b. Indentations 608 formed in article 601 can plastically deform the first layer 604a, second layer 604b, and the substrate 602 creating stressed region 610. A delamination force at stressed region 610 can cause delamination of second layer 604b, or both second layer 604b and first layer 604a, at or near stressed region 610. Delamination of both second layer 604b and first layer 604a is evidence by exposed portion 612 of underlying substrate 602. If only some of second layer 604b is delaminated, a corresponding portion of underlying first layer 604a will be visible.

Figure 7:
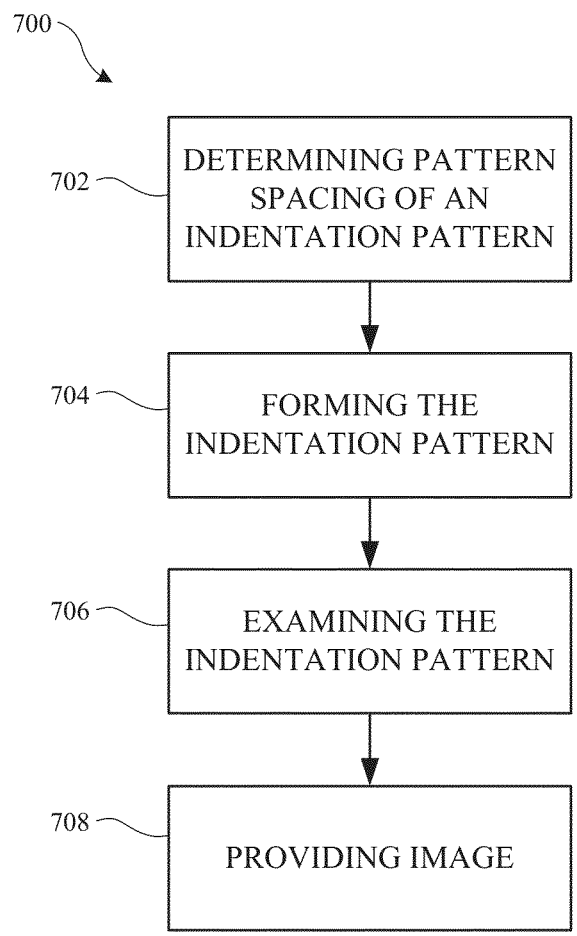
FIG. 7 is a flow diagram depicting a method of testing a coating for adhesion integrity.

FIG. 7 is a flow diagram 700 depicting a method of testing a coating for adhesion integrity in accordance with some embodiments. At 702, a pattern spacing of an indentation pattern is determined. Desired indentation shape, orientation, size, depth and spacing (distance between indentations) can depend on the hardness of the coating(s), the hardness of the substrate, the shape and size of the indenting tool, and the force used to form the indentations. Spacing between the indentations may depend on the size and shape of the indentations, in addition to the type and hardness of the coating and substrate. For example, in some applications a spacing that is less than about three times a diameter of substantially equally sized indentations provides optimal results.

At 704, the determined indentation pattern is formed on an article. In some embodiments the surface of the article is substantially flat and the indenter is pressed into the surface of the article in a direction substantially perpendicular to the surface of the article. Maintaining a flat surface on the article and perpendicular force on the indenter can ensure that the indentations are symmetric in shape. In some embodiments, the indenting tool applies force for 10 seconds. An array or grid of symmetric indentations may ensure reliable and repeatable evaluations of a coating. Stressed regions are formed in the interstices between the indentations, which correspond to locations where delamination is likely to occur.

At 706, the indentation pattern that is formed on the article is examined. In some embodiments an optical image of the indentation pattern is created. An optical image can show delamination of coating that optically contrasts with the substrate. In other embodiments, a scanning electron microscope (SEM) image is used. SEM may be required where there is little optical contrast, such as for some non-dyed or light-colored anodic oxide coatings. However, darker dyed anodic oxide coatings may have enough optical contrast with the underlying metal substrate to use optical imaging techniques. In some embodiments, multiple images are stitched together to provide a single image of the indentation pattern.

At 708, an image is provided detailing the level of delamination. The image can be in the form of a picture or image displayed on a computer screen. The image can be analyzed, either by an operator or automatically using image analyzing techniques. In some embodiments, the number of stressed regions that experience delamination is counted and compared to similar articles to obtain objective results as to adhesion performance of different coatings. In some embodiments, a total area of delamination is determined as a measure of the extent of delamination.

Figure 8:
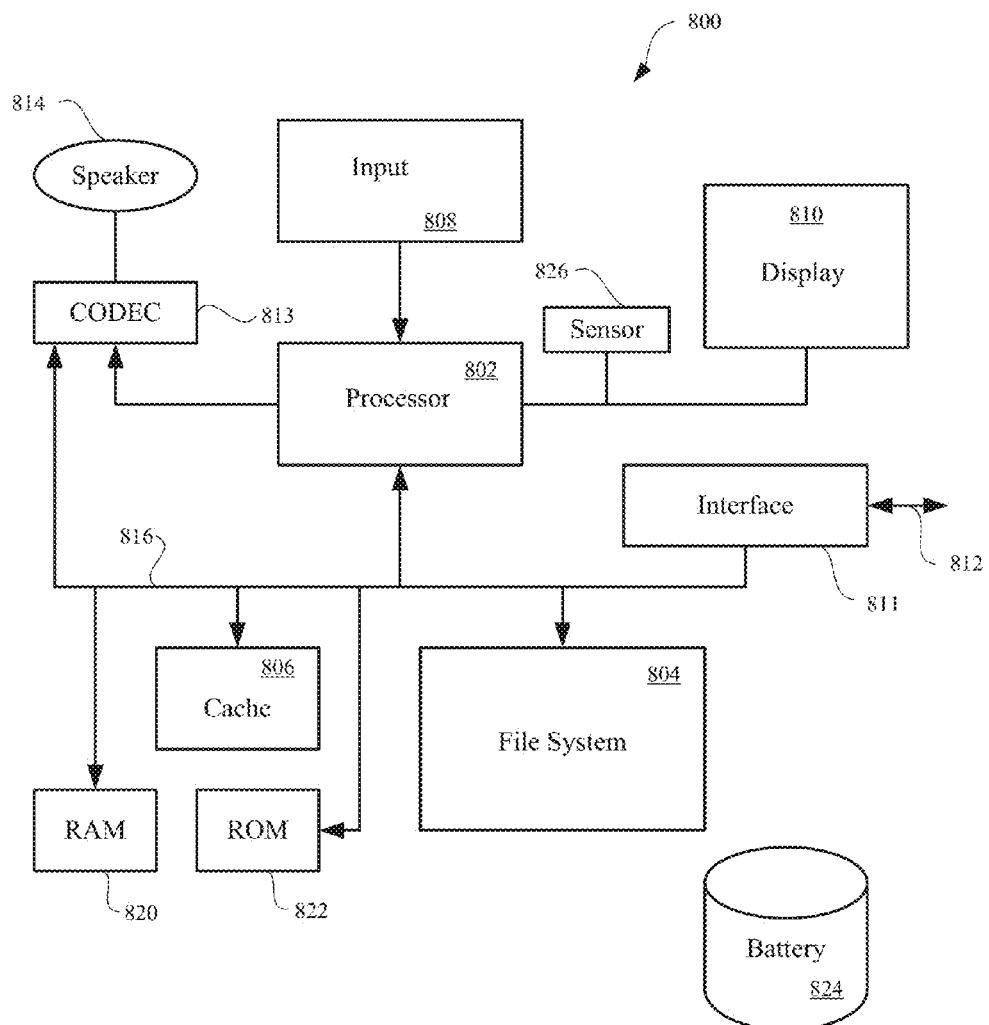
FIG. 8 is a block diagram of an electronic device suitable for use with the described embodiments.

FIG. 8 is a block diagram of electronic system 800 suitable for controlling some of the indentation testing processes described above. Electronic system 800 can represent a computing system as part of an indentation machine such as a Vickers hardness testing machine. Electronic system 800 includes a processor 802 that pertains to a microprocessor or controller for controlling the overall operation of electronic system 800. Electronic system 800 contains instruction data pertaining to manufacturing instructions in a file system 804 and a cache 806. The file system 804 is, typically, a storage disk or multiple disks. The file system 804 typically provides high capacity storage capability for the electronic system 800. However, since the access time to the file system 804 can be relatively slow, electronic system 800 can also include a cache 806. Cache 806 can be, for example, Random-Access Memory (RAM) provided by semiconductor memory. The relative access time to the cache 806 can be substantially shorter than for the file system 804. However, cache 806 may not have the large storage capacity of the file system 804. Further, file system 804, when active, can consume more power than cache 806. The power consumption is often a concern when the electronic system 800 is a portable device that is powered by a battery 824. The electronic system 800 can also include a RAM 820 and a Read-Only Memory (ROM) 822. ROM 822 can store programs, utilities or processes to be executed in a non-volatile manner. RAM 820 can provide volatile data storage, such as for cache 806.

Electronic system 800 can also include a user input device 808 that allows a user of the electronic system 800 to interact with the electronic system 800. For example, a user input device 808 can take a variety of forms, such as a button, keypad, dial, touch screen, audio input interface, visual/image capture input interface, input in the form of sensor data, etc. Still further, the electronic system 800 can include a display 810 (screen display) that can be controlled by the processor 802 to display information to the user. As described above, in some embodiments, display 810 provides images collected from an optical imaging tool and/or a scanning electron microscope. Data bus 816 can facilitate data transfer between at least the file system 804, the cache 806, the processor 802, and a coder/decoder (CODEC) 813. CODEC 813 can be used to decode and play multiple media items from file system 804 that can correspond to certain activities taking place during a particular manufacturing process. Processor 802, upon a certain manufacturing event occurring, supplies the media data (e.g., audio file) for the particular media item to a CODEC 813. CODEC 813 can then produce analog output signals for a speaker 814. Speaker 814 can be a speaker internal to electronic system 800 or external to electronic system 800. For example, headphones or earphones that connect to the electronic system 800 would be considered an external speaker.

Electronic system 800 can also include a network/bus interface 811 that couples to a data link 812. Data link 812 can allow electronic system 800 to couple to a host computer or to accessory devices. Data link 812 can be provided over a wired connection or a wireless connection. In the case of a wireless connection, network/bus interface 811 can include a wireless transceiver. The media items (media assets) can pertain to one or more different types of media content. In one embodiment, the media items are audio tracks (e.g., songs, audio books, and podcasts). In another embodiment, the media items are images (e.g., photos). However, in other embodiments, the media items can be any combination of audio, graphical or visual content. Sensor 826 can take the form of circuitry for detecting any number of stimuli. For example, sensor 826 can include any number of sensors for monitoring a manufacturing operation such as for example a Hall Effect sensor responsive to external magnetic field, an audio sensor, a light sensor such as a photometer, and so on.

The various aspects, embodiments, implementations or features of the described embodiments can be used separately or in any combination. Various aspects of the described embodiments can be implemented by software, hardware or a combination of hardware and software. The described embodiments can also be embodied as computer readable code on a non-transitory computer readable medium for controlling manufacturing operations or as computer readable code on a non-transitory computer readable medium for controlling a manufacturing line. The non-transitory computer readable medium is any data storage device that can store data, which can thereafter be read by a computer system. Examples of the non-transitory computer readable medium include read-only memory, random-access memory, CD-ROMs, DVDs, magnetic tape, optical data storage devices, and carrier waves. The non-transitory computer readable medium can also be distributed over network-coupled computer systems so that the computer readable code is stored and executed in a distributed fashion.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not target to be exhaustive or to limit the embodiments to the precise forms disclosed. It will be apparent to one of ordinary skill in the art that many modifications and variations are possible in view of the above teachings.

What is claimed is:

1. A method of determining an adhesion strength between a metal substrate and a coating that overlays the metal substrate, the method comprising:
    forming indentations extending through the coating and into the metal substrate by applying a pre-defined amount of impact force to a region of the coating using an impact agent, wherein at least two of the indentations are capable of generating residual stresses commensurate with a stress induced by the impact force at the region, and the residual stresses combine to form a detachment force that, when greater than the adhesion strength, is capable of causing a separation of the coating and the metal substrate at the region.

2. The method of claim 1, wherein the at least two indentations are separated by a pre-defined distance that is sufficient for physical communication with each other at the region.

3. The method of claim 2, wherein the pre-defined distance between the at least two indentations is less than three times an average diameter of the at least two indentations.

4. The method of claim 1, wherein the indentations are arranged according to an array of rows and columns.

5. The method of claim 1, wherein the pre-defined amount of impact force is constant.

6. The method of claim 1, wherein the pre-defined amount of impact force is individually adjustable.

7. The method of claim 1, further comprising:
    determining a portion of the coating that is separated from the metal substrate at the region.

8. The method of claim 1, wherein the region is defined by edges of the indentations.

9. The method of claim 1, wherein the impact agent includes an indenting tool having a symmetric shape that is capable of forming corresponding symmetrically shaped indentations.

10. The method of claim 1, wherein the impact agent has a mass that is between 500 grams to 50 kilograms.

11. The method of claim 1, wherein the metal substrate is at least one of aluminum or aluminum alloy, and the coating is aluminum oxide.

12. A method of determining an adhesion strength between a metal substrate and a coating disposed over the metal substrate, the method comprising:
forming indentations within the coating and the metal substrate, wherein the indentations include at least a first indentation and a second indentation that are separated by a pre-defined distance that is sufficient to cause a first amount of strain generated by the first indentation to physically communicate with a second amount of strain generated by the second indentation to form a delamination force at a region of the coating, and wherein the coating delaminates from the metal substrate at the region when the delamination force is greater than the adhesion strength.

13. The method of claim 12, wherein the indentations are formed by an impacting agent having a mass that ranges between 500 grams to 50 kilograms.

14. The method of claim 12, wherein the first and second indentations are adjacent to each other.

15. The method of claim 12, wherein the indentations are formed by using an indentation tool arranged to deliver a pre-defined amount of impact force on the coating and the substrate.

16. The method of claim 12, wherein the indentations are formed within the coating and the metal substrate by an indentation tool that delivers a pre-defined amount of impact force in a direction that is generally perpendicular to a surface of the coating.

17. A system for determining an adhesion strength between a substrate and a coating that overlays the substrate, the system comprising:
an indentation tool arranged to form indentations extending through the coating and the substrate by applying a pre-defined amount of impact force at a region of the coating, wherein at least two of the indentations formed by the indentation tool are capable of physically communicating with each other to form a detachment force that, when greater than the adhesion strength, is capable of causing a portion of the coating to separate from the substrate; and
an image processing component capable of determining the portion of the coating that separates from the substrate.

18. The system of claim 17, wherein the indentation tool delivers the pre-defined amount of impact force in a direction that is generally perpendicular to a surface of the coating.

19. The system of claim 17, wherein the indentation tool is capable of adjusting the pre-defined amount of impact force for the indentations.

20. The system of claim 17, wherein the indentations are arranged according to an array of rows and columns.

* * * * *